(12) United States Patent
Mallory et al.

(10) Patent No.: US 11,497,468 B2
(45) Date of Patent: Nov. 15, 2022

(54) ULTRASOUND PROBE

(71) Applicant: FUJIFILM SONOSITE, INC., Bothell, WA (US)

(72) Inventors: Robert Mallory, Bothell, WA (US); Gregg Frey, Bothell, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 154 days.

(21) Appl. No.: 16/230,870

(22) Filed: Dec. 21, 2018

(65) Prior Publication Data

US 2020/0196985 A1 Jun. 25, 2020

(51) Int. Cl.
*A61B 8/00* (2006.01)
*F28F 3/04* (2006.01)

(52) U.S. Cl.
CPC .......... *A61B 8/4444* (2013.01); *A61B 8/4455* (2013.01); *A61B 8/4494* (2013.01); *A61B 8/546* (2013.01); *F28F 3/048* (2013.01)

(58) Field of Classification Search
CPC ..... A61B 8/4444; A61B 8/4494; A61B 8/546; A61B 8/4461; A61B 8/4455; F28F 3/048
See application file for complete search history.

(56) References Cited

U.S. PATENT DOCUMENTS

| 4,628,406 A * | 12/1986 | Smith | H01L 23/5387 361/795 |
|---|---|---|---|
| 5,602,718 A | 2/1997 | Peszynski | |
| 8,253,368 B2 * | 8/2012 | Landry | A47L 9/2831 701/28 |
| 2003/0207499 A1 * | 11/2003 | DiStefano | H01L 24/86 257/E23.125 |
| 2004/0228781 A1 * | 11/2004 | Tonkovich | F28F 3/048 422/177 |

(Continued)

FOREIGN PATENT DOCUMENTS

| DE | 69628901 T2 | 8/2003 |
|---|---|---|
| JP | 2006204552 | 8/2006 |

(Continued)

OTHER PUBLICATIONS

Japanese Office Action and Search Report on the Patentability of Application No. 2021-534751 dated May 26, 2022, 2 pages.

(Continued)

*Primary Examiner* — Joseph M Santos Rodriguez
*Assistant Examiner* — Kaitlyn E Sebastian
(74) *Attorney, Agent, or Firm* — Womble Bond Dickinson (US) LLP

(57) ABSTRACT

An ultrasound probe and method for using the same are described. In one embodiment, the ultrasound probe comprises: a probe array assembly having a probe tip; a first enclosure disposed around a portion of the probe array assembly, where the first enclosure has first and second openings and comprises a thermally conductive material; and one or more thermally conductive fins contained within the first enclosure, each of the one or more thermally conductive fins having one end enclosed within the probe array assembly and a portion extending away from the probe array assembly and in thermal contact with an inner surface of the first enclosure to create a thermal path from the first opening to the second opening in the first enclosure.

19 Claims, 12 Drawing Sheets

(56) References Cited

U.S. PATENT DOCUMENTS

| | | | | |
|---|---|---|---|---|
| 2008/0111234 | A1* | 5/2008 | Hua | H01L 23/4275 428/221 |
| 2008/0146924 | A1* | 6/2008 | Smith | G01S 7/52017 601/2 |
| 2012/0150038 | A1* | 6/2012 | Osawa | A61B 8/4444 600/443 |
| 2014/0058270 | A1* | 2/2014 | Davidsen | A61B 8/4494 600/459 |
| 2015/0087988 | A1* | 3/2015 | Lee | B06B 1/0622 600/459 |
| 2016/0061650 | A1* | 3/2016 | Sato | G01N 29/2418 73/655 |
| 2016/0174939 | A1* | 6/2016 | Cho | B06B 1/0629 600/459 |
| 2017/0164926 | A1* | 6/2017 | Spicci | A61B 8/4444 |
| 2018/0078240 | A1* | 3/2018 | Pelissier | A61B 8/4444 |
| 2018/0271372 | A1* | 9/2018 | Lee | A61B 5/0035 |

FOREIGN PATENT DOCUMENTS

| | | |
|---|---|---|
| JP | 2013052023 | 3/2013 |
| JP | 2017093878 | 6/2017 |
| JP | 2017104203 A | 6/2017 |
| WO | 2014080312 | 5/2014 |

OTHER PUBLICATIONS

International Search Report for Application No. PCT/US2019/066099 dated Apr. 10, 2020. (7 pages).

International Preliminary Report and Written Opinion on the Patentability of Application No. PCT/US2019/066099 dated Jul. 1, 2021, 8 pages.

Extedned European Search report on the Patentability of Application No. 19898851.1 dated Jul. 11, 2022, 7 pages.

* cited by examiner

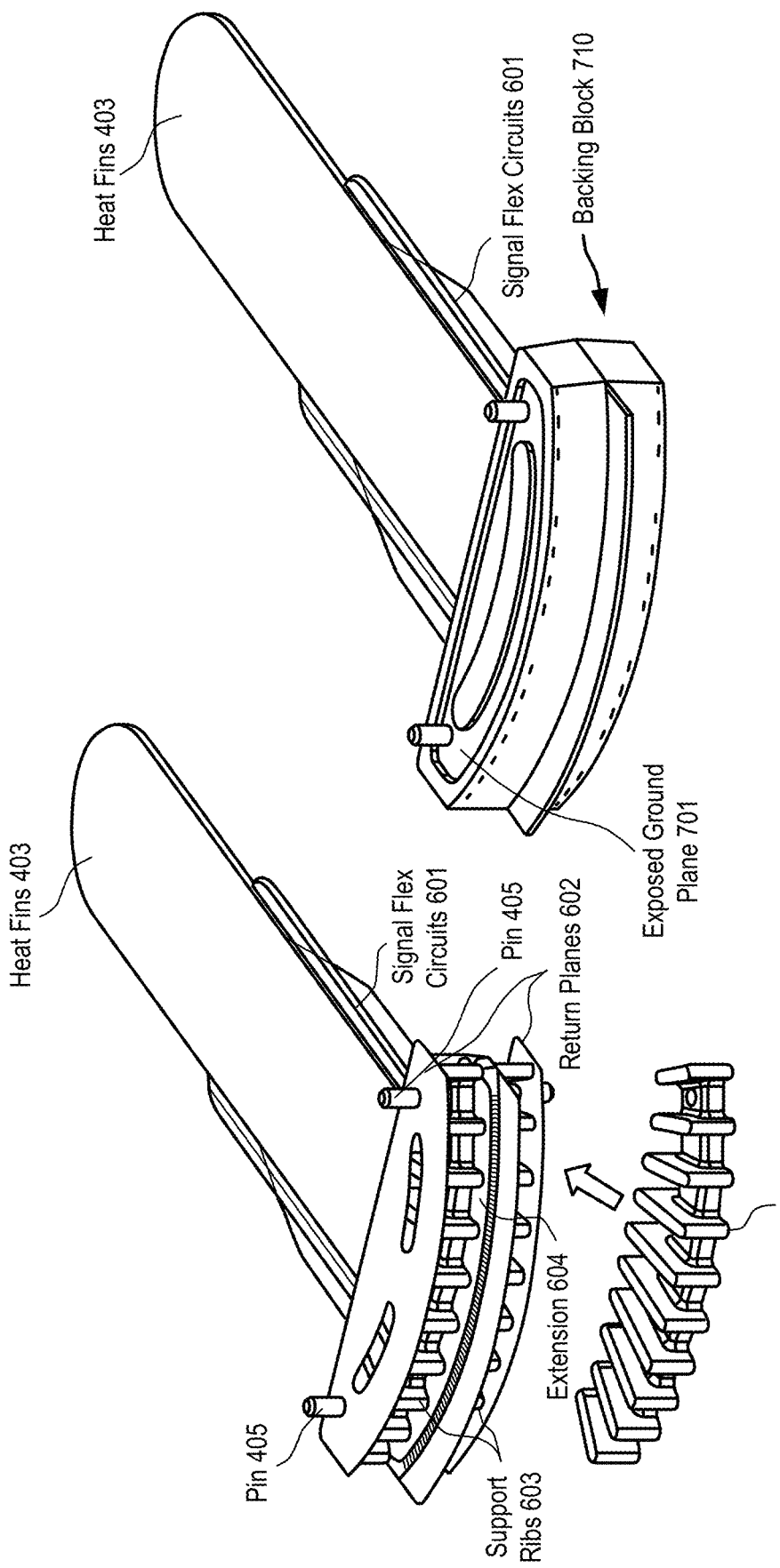

Heat concentrated near tip.

More heat transferred to probe handle.

ULTRASOUND PROBE

FIELD OF THE INVENTION

The present invention relates generally to ultrasound transducer; more specifically, the present invention relates to ultrasound transducer assemblies that include thermally conductive fins or planar layers in an ultrasound transducer assembly.

BACKGROUND

Transducers, such as acoustic transducers, are used in medical imaging where an acoustic probe transmits and receives ultrasound waves to create images of the internal tissues of a patient. Generally, it is desirable to use the acoustic probe at a maximum permissible acoustic intensity to enable higher quality imaging, which may be achieved via better penetration of the acoustic waves into the patient's tissues. However, operating the acoustic probe at higher acoustic intensities may result in excessive heat being generated in the transducer assembly.

Limits exist on the maximum external temperature of an acoustic probe at points of contact with the patient. In certain modes of operation of the acoustic probe, the heat generated within the transducer elements or its assembly may cause the temperature of some regions of the probe surface to exceed permissible limits.

Transducer assemblies are generally fabricated employing materials with lower intrinsic thermal conductivity or that utilize short, thin cross-sectional thermal components, which are for limited conduction away from heat-producing components, and limited conduction to the outer shell. Such transducer assemblies may result in the overheating of the probe. Disadvantageously, many previous attempts to enhance the thermal conductivity of the acoustic probe have had limited effect on the face temperature of the probe and therefore may be ineffective in sufficiently reducing the face temperature enough to prevent discomfort to a patient.

Thus, it is desirable to dissipate the heat that may be trapped in the array of transducer elements in order to circumvent the overheating of the patient contact surfaces of the transducer assembly.

SUMMARY OF THE INVENTION

An ultrasound probe and method for using the same are described. In one embodiment, the ultrasound probe comprises: a probe array assembly having a probe tip; a first enclosure disposed around a portion of the probe array assembly, where the first enclosure has first and second openings and comprises a thermally conductive material; and one or more thermally conductive fins contained within the first enclosure, each of the one or more thermally conductive fins having one end enclosed within the probe array assembly and a portion extending away from the probe array assembly and in thermal contact with an inner surface of the first enclosure to create a thermal path from the first opening to the second opening in the first enclosure.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

FIGS. 6A-6B and 7A-7B illustrate embodiments of the backing block with heat fins.

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

An ultrasound transducer probe having a transducer assembly and system for using the same are disclosed. Embodiments of the ultrasound transducer probe offers one or more improvements over probes of the prior art. First, the probe construction greatly improves thermal management, provides enhanced electromagnetic interface (EMI) control, and increased structural integrity. These improvements have been achieved while eliminating many labor-intensive production processes which are often subject to human error, such as, for example, hand casting, hand-wrapping components with copper foil and soldering around electrical components. Because many labor-intensive production processes have been eliminated, embodiments of the ultrasound transducer probe provide for more repeatable production steps without batch variations, which cut production assembly time significantly.

Figure 1:
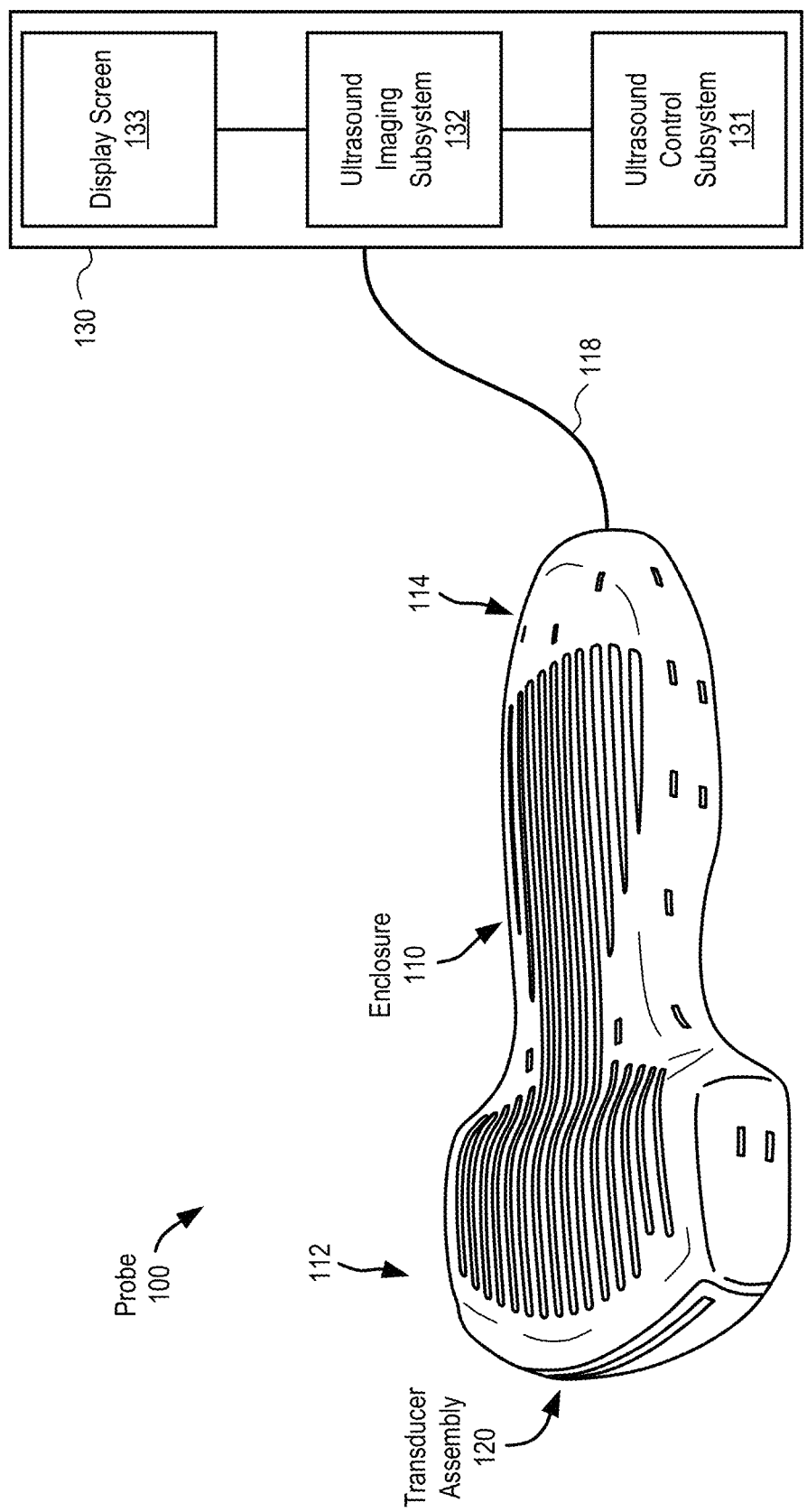
FIG. 1 illustrates one embodiment of an ultrasound transducer probe having an ultrasound transducer assembly.

FIG. 1 illustrates one embodiment of an ultrasound transducer probe having an ultrasound transducer assembly configured in accordance with an embodiment of the disclosed technology. Referring to FIG. 1, ultrasound transducer probe 100 includes an enclosure 110 extending between a distal end portion 112 and a proximal end portion 114. In one embodiment, enclosure 110 of ultrasonic transducer probe 100 has a transparent cover that surrounds an inner shell. In one embodiment, the inner shell comprises of metal material (e.g., diecast aluminum, etc.). In one embodiment, the transparent cover comprises transparent plastic (e.g., polysulfone) overmolded on the die cast metal inner shell. In one embodiment, the outer cover and the inner shell create enclosure 110 and work together to transfer heat out of the probe.

Enclosure 110 is configured to carry or house system electronics (e.g., one or more processors, integrated circuits, application-specific integrated circuits (ASICs), field programmable gate arrays (FPGAs), beamformers, batteries and/or other power sources) disposed in an interior portion or cavity of enclosure 110. The system electronics (not shown) are electrically coupled to an ultrasound imaging system 130 via a cable 118 that is attached to the proximal end of the probe.

At the probe tip, a transducer assembly 120 having one or more transducer elements is electrically coupled to the system electronics. In operation, transducer assembly 120 transmits ultrasound energy from the one or more transducer elements toward a subject and receives ultrasound echoes from the subject. The ultrasound echoes are converted into electrical signals by transmit receive circuitry and electrically transmitted to the system electronics and to electronics (e.g., one or more processors, memory modules, beamformers, FPGAs, etc.) in ultrasound imaging system 130 configured to process the electrical signals and form one or more ultrasound images.

Capturing ultrasound data from a subject using an exemplary transducer assembly (e.g., the transducer assembly 120) generally includes generating ultrasound, transmitting ultrasound into the subject, and receiving ultrasound reflected by the subject. A wide range of frequencies of ultrasound may be used to capture ultrasound data, such as, for example, low frequency ultrasound (e.g., less than 15 MHz) and/or high frequency ultrasound (e.g., greater than or equal to 15 MHz) can be used. Those of ordinary skill in the art can readily determine which frequency range to use based on factors such as, for example, but not limited to, depth of imaging and/or desired resolution.

In one embodiment, ultrasound imaging system 130 includes ultrasound control subsystem 131 having one or more processors. At least one processor causes electrical currents to be sent to the transducer(s) of probe 100 to emit sound waves and also receives the electrical pulses from the probe that were created from the returning echoes. A processor processes the raw data associated with the received electrical pulses and forms an image that is sent to ultrasound imaging subsystem 132, which displays the image on display screen 133. Thus, display screen 133 displays ultrasound images from the ultrasound data processed by the processor of ultrasound control subsystem 131.

In one embodiment, the ultrasound system also has one or more user input devices (e.g., a keyboard, a cursor control device, etc.) that inputs data and allows the taking of measurements from the display of the ultrasound display subsystem, a disk storage device (e.g., hard, floppy, compact disks (CD), digital video discs (DVDs)) for storing the acquired images, and a printer that prints the image from the displayed data. These also have not been shown in FIG. 1 to avoid obscuring the techniques disclosed herein.

In one embodiment, the ultrasound transducer probe has integrated components for improved thermal management, electromagnetic interference (EMI) mitigation and structural integrity. The thermal properties are achieved by encapsulating long heat fins within the probe. These heat fins extend into the handle of the ultrasonic probe to transfer heat away from the heat producing components in the probe tip. The thermal transfer is further enhanced by a highly conductive inner enclosure (e.g., a metal enclosure, an enclosure comprising ceramic or other materials that offer both improved thermal and structural integrity) which contacts the long heat fins and conducts heat from the heat fins to the outer surface of the transducer probe. In one embodiment, the inner case has overlapping joints between halves of the enclosure for additional structural integrity, as well as EMI control. In one embodiment, an outer surface of the probe includes a plastic case that encapsulates the inner enclosure. The outer plastic case offers protection against electrical hazards, liquid ingress, and cosmetic damage.

In one embodiment, ultrasound transducer probe 100 comprises a probe array assembly having a probe tip, a first enclosure disposed around a portion of the probe array comprising a thermally conductive material (e.g., metal (e.g., diecast aluminum), etc.), and one or more thermally conductive heat fins contained within the first enclosure. In one embodiment, each thermally conductive heat fin has an end enclosed within the probe array assembly and has a portion that extends away from the probe array assembly (e.g., a planar extension) that is in thermal contact with an inner surface of the first enclosure to transfer heat from the probe tip located proximally to one opening in the first enclosure. In one embodiment, material within ultrasound transducer probe 100 (e.g., elastomer or other foam pads) forces the heat fins toward and in contact with the inner surface of the first enclosure.

In one embodiment, a second enclosure (e.g., an overmolded plastic enclosure), or cover, is disposed around the first enclosure and operates to overlap and cover a substantial portion, if not all, of the outside surface of the first enclosure. In one embodiment, the first enclosure comprises top and bottom clamshell halves and the second enclosure comprise top and bottom clamshell halves. The top clamshell half of the second enclosure is coupled to and overlaps the top clamshell half of the first enclosure, while the bottom clamshell half of the second enclosure is coupled to and overlaps the bottom clamshell half of the first enclosure. In one embodiment, the coupling between these respective clamshell halves is accomplished, at least in part, using mechanical interlocks.

Embodiments of enclosure 110 provide a number of features. In one embodiment, the features include one or more of improved heat transfer, an electromagnetic compatibility (EMC) Faraday cage (to the extent possible with a probe tip), a ruggedized structural enclosure, and a simple final assembly. For example, using one or more of these features, embodiments of ultrasound transduce probe 100 have been shown to provide a decrease of 1.2° C. or more improvement at the probe tip of other probes.

Figure 2:
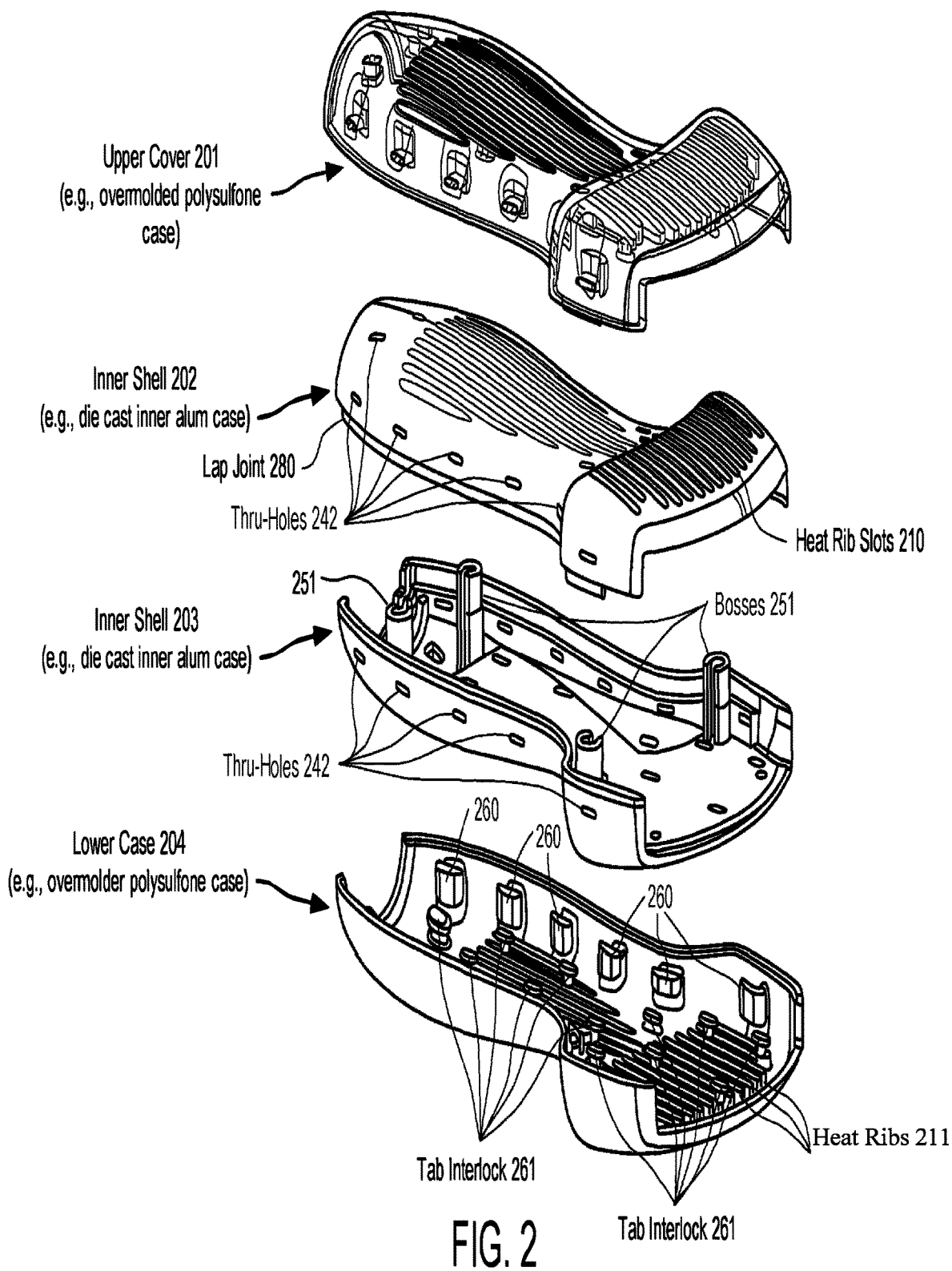
FIGS. 2 and 3 illustrate one embodiment of a probe case.
Figure 3:
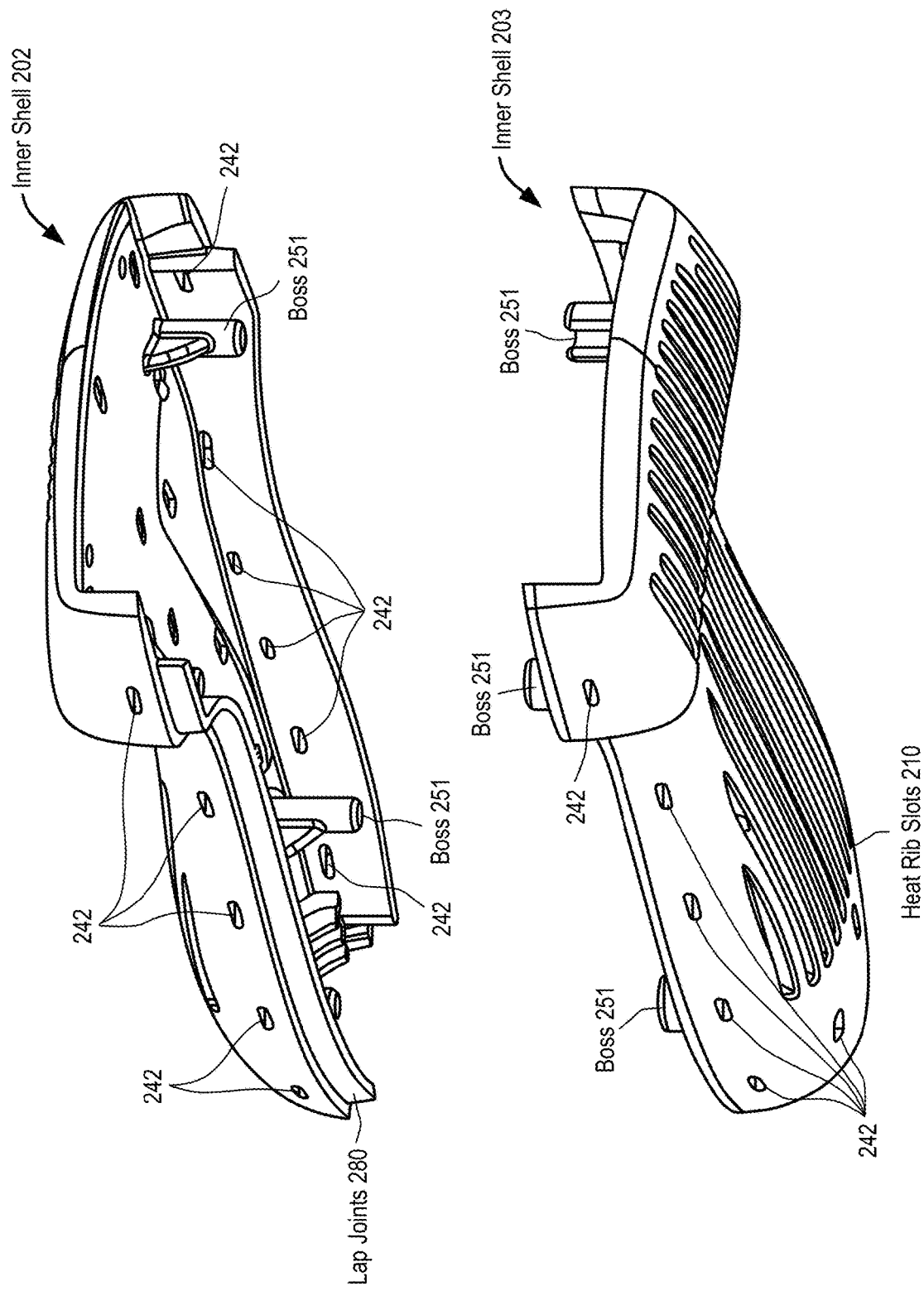

FIGS. 2 and 3 illustrate one embodiment of a probe case. In one embodiment, the probe case comprises an upper pair of clamshell halves consisting of upper cover 201 and inner shell 202 and a lower pair of clamshell halves consisting of lower cover 204 and inner shell 203. Inner shell 202 and inner shell 203 are coupled together to form a first enclosure and upper cover 201 and lower cover 204 are coupled together to form second enclosure that covers a substantial portion of the outer surface of the first enclosure. In one embodiment, the combined enclosures operate as a housing that includes a handle portion at the end having the cable assembly for the ultrasound transducer probe (e.g., the distal end 114 of FIG. 1) and the transducer array housing near the other end (e.g., the proximal end 112 of FIG. 1).

In one embodiment, inner shell 202 and inner shell 203 comprise a thermally conductive material. In one embodiment, inner shell 202 and inner shell 203 also comprise an electrically conductive material, such as, for example, but not limited to, a die cast aluminum, other metals, composite alloys, etc. Inner shell 202 and inner shell 203 may comprise other metal materials or non-metal materials (e.g., ceramic). Note that as a die cast aluminum inner shell case, the first enclosure created by inner shell 202 and inner shell 203 provides structural integrity, provides thermal transfer from heat fins (as described later) and acts as an EMC enclosure, such that no copper foil is needed for the electronics. In alternative embodiments, inner shell 202 and 203 are created using methods other than die casting, such as, for example, but not limited to, well-known methods such as pressure forming, investment casting, computerized numerical control (CNC) milling, or less well-known methods.

In one embodiment, upper cover 201 and lower cover 204 are coupled together to form an overmolded plastic case (e.g., an injection molded polysulfone case). Note that upper cover 201 and lower cover 204 may comprise materials other than overmolded polysulfone, such as, for example, but not limited to, a polymer material, an insulate material, etc.

In one embodiment, upper cover 201 and lower cover 204 are permanently overmolded onto inner shell 202 and inner shell 203, respectively. In one embodiment, inner shell 202 includes a number of thru-holes, such as for example, thru-holes 242. In one embodiment, when inner shell 202 is coupled to and enclosed within (e.g., covered by) upper cover 201 and inner shell 203 is coupled to and enclosed within (e.g., covered by) lower cover 204, the plastic that is injection molded to form upper cover 201 and lower cover 204 proceeds through thru-holes 242 and injection molded tab interlocks are formed on the opposite side of inner shell 202 and inner shell 203. These tab interlocks hold upper cover 201 to inner shell 202 and hold inner shell 203 to lower cover 204. That is, in one embodiment, injection molding of the outer cover (upper cover 201 and lower cover 204) is allowed to go through thru-holes 242 in halves of the inner enclosure (e.g., a metal case) and overlap in the interior of the inner enclosure, thereby creating tab interlocks that form a mechanical interlock between the outer cover formed by upper cover 201 and lower cover 204 and the inner enclosure formed by inner shell 202 and inner shell 203. The mechanical interlock produced by thru-holes 242 provides a strong mechanical lock to keep the plastic from delaminating.

Examples of such tab interlocks are shown as tab interlocks 260 and 261 in lower cover 204. The tab interlocks will be shown in additional figures described in more detail below.

In one embodiment, inner shell 202 and inner shell 203 are coupled together using lap joint 280 and one or more bosses (e.g., C-bosses) to form a metal case that connects with the cable enclosure at the end of the ultrasound transducer probe. In one embodiment, lap joint 280 provides EMC integrity (e.g., prevents leakage of electromagnetic waves) and structural integrity, such that when coupled together, a substantially complete Faraday cage is created except for the acoustic portion of the transducer at the front opening (at the proximal end) and rear opening (at the distal end). In one embodiment, a more complete Faraday cage is created where the lens includes an additional electrically conductive path that is connected to a gasket in the transducer assembly. In such a case, the gasket is coupled to at least one heat fin extending into the probe handle. Examples such a gasket and heat fin are EMI gasket 401 and heat fins 403 of FIG. 4 which are described in more detail below. In one embodiment, this electrically conductive path comprises a foil embedded in the lens. In another embodiment, this electrically conductive path comprises a metal overlay (e.g., sputtered metal) that is over a portion of the transducer.

In one embodiment, there are four bosses 251 that couple inner shell 202 and inner shell 203 together via a compliant interference fit, though more or less than 4 bosses may be used. In one embodiment, bosses 251 are C-bosses that include solid bosses with ribs that mate with hollow C-bosses. The bosses provide precision alignment, structural interlock, compliant tolerance allowance, and a larger surface area.

In one embodiment, upper cover 201 and/or lower cover 204 include heat ribs. Examples of heat ribs are shown as heat ribs 211 in lower cover 204. In one embodiment, there are multiple heat ribs that protrude and extend up from the inner surface of lower cover 204, or protrude and extend down from the inner surface of upper cover 201. When upper cover 201 is coupled to inner shell 202, the heat ribs extend into heat rib slots, such as heat rib slots 210, on inner shell 202. In one embodiment, similar heat rib slots are included in inner shell 203. The heat rib slots knit upper cover 201 to inner shell 202 and knit inner shell 203 to lower cover 204 to enhance heat transfer and structural integrity. The size of the heat ribs and/or the heat rib slots varies for different embodiments. However, increasing the surface area of the heat ribs and/or heat slots and reducing the spacing of the heat ribs and/or heat slots to make a tight or closer fit increases thermal transfer. Therefore, the surface area and the spacing of the heat ribs and/or heat slots may be adapted or optimized for different transducers operating at different frequencies, to control temperature reductions associated with the different transducers. In one embodiment, to transfer heat more efficiently, the heat ribs are increased in size to have more surface area when using transducers of higher frequency.

FIG. 3 illustrates another view of inner shell 202 and inner shell 203. As shown, inner shell 202 includes thru-holes 242 to provide holes for an injection molded material used to secure inner shell 202 to upper cover 201 (FIG. 2) and inner shell 203 to lower cover 204. As shown, inner shell 203 includes heat rib slots 210 to receive heat ribs protruding from lower cover 204 (as is the case with heat rib slots of inner shell 202 receiving heat ribs protruding from upper cover 201) and provide thermal transfer from heat fins within the probe (described in more detail below in conjunction with FIGS. 4 and 6A-10) to the outer surface of the ultrasonic transducer probe.

Figure 4:
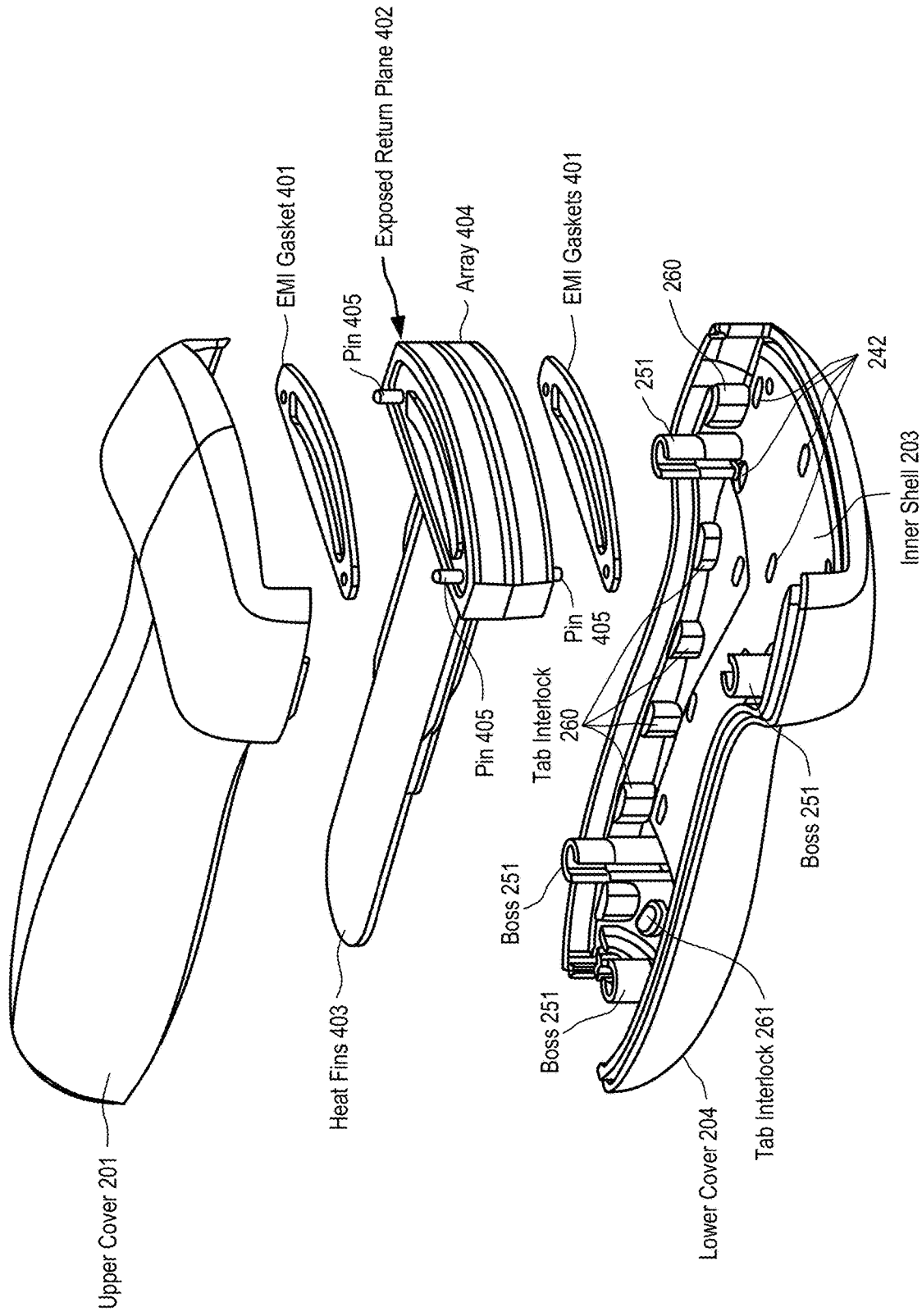
FIG. 4 illustrates one embodiment of a probe case of an ultrasonic transducer probe near final assembly.

FIG. 4 illustrates one embodiment of a probe case of an ultrasonic transducer probe near final assembly. Referring to FIG. 4, upper cover 201 is attached to and covers an outer surface of inner shell 202, and lower cover 204 is attached to and covers an outer surface of inner shell 203. In one embodiment, inner shell 203 has overlapped joints with lower cover 204 and inner shell 202 has overlapped joints with upper cover 201 such that when the integrated halves are coupled together, a substantially complete Faraday cage is created (except for the front and rear openings of the ultrasonic probe). As discussed above, thru-holes 242 in inner shell 202 and inner shell 203 allow for plastic flow to create a mechanical interlock between inner shell 202 and upper cover 201 and between inner shell 203 and upper cover 204. Note that in one embodiment, the shape of thru-holes 242 to create the tab interlocks depends on the material being used for the over molding of the covers (e.g., upper cover 201, lower cover 204). If the material for the over molding is more viscous, the shape of thru-holes 242 may require a larger diameter. Also, in one embodiment, the width-to-thickness ratio is chosen for the shape of thru-holes 242 to ensure the diameter of thru-holes 242 permits flow through of the over molding material.

The ultrasonic transducer probe also includes a transducer array 404 that includes the transducer elements. In one embodiment, array 404 is injection molded. This eliminates the need to the labor-intensive and error-prone hand casting. Array 404 includes exposed return plane 402 that mates with EMI gaskets 401 on the top and bottom of array 404. In one embodiment, exposed return plane 402 comprises a metal such as, but not limited to, copper. In one embodiment, EMI gaskets 401 are coupled to the array 404 via pins 405. In one embodiment, exposed return plane 402 couples directly with the EMI gaskets 401. In one embodiment, EMI gaskets 401 are electrically conductive and make contact the inner surface of the first enclosure created by inner shell 202 and inner shell 203. By doing so, EMI gaskets 401 allow direct contact from return plane 402 of array 404 to the inner shells 202 and 203.

In one embodiment, the ultrasound transducer probe also includes one or more thermally conductive heat fins, such as heat fins 403. In one embodiment, heat fins 403 include a pair of heat fins that comprise a thermally conductive material (e.g., copper, aluminum, etc.) or another material that thermally conducts heat away from the probe tip. In alternative embodiments, only one heat fin or more than two heat fins are included. In one embodiment, each of heat fins 403 has one end enclosed within the portion of the transducer array assembly that contains array 404. In one embodiment, the backing block for array 404 includes not only the flex circuits but also heat fins 403 which are embedded in the backing block. In one embodiment, each of heat fins 403 includes a flat planar section (e.g., a planar extension) that extends from away from the probe array assembly having array 404 toward the handle, or distal portion (114), of the ultrasound transducer probe. In one embodiment, heat fins 403 extend to a location in the probe near where the cable in the cable assembly is exposed away from its wire mesh. In cases where there is direct or indirect contact between heat fins 403 and the cable, a highly conductive cable may improve the thermal transfer from the transducer face through the full length of the probe.

At least a portion of the planar extension of each of heat fins 403 is in thermal contact with the interior surface of the enclosure created by coupling inner shells 202 and 203. As inner shells 202 and 203 are thermally conductive, in one embodiment, heat fins 403 transfer heat from the probe tip where array 404 is located at the proximal end (112) to inner shells 202 and 203 and ultimately to the outer portion/exposed cable assembly of the probe that includes portions of the cover created by upper cover 201 and lower cover 204. That is, in one embodiment, the thermal transfer occurs from one end of the probe enclosure to the other end of the probe enclosure. In one embodiment, heat fins 403 are embedded in the backing block to extend to within the eighteen to twenty thousandths of an inch of the probe tip and conduct heat from the probe tip all the way to the back of the probe handle. Note that the heat transfer not only occurs in the x and y axis spanning the plane of a heat fin but as well as the z axis which is perpendicular to the heat fin. This enables thermal transfer towards the outer surface of the enclosure created by inner shells and outer covers.

In one embodiment, heat fins 403 are forced into thermal contact with the inner surface of inner shells 202 and 203 using one or more pads (e.g., elastomer foam pads) or one or more other internal structures or mechanisms. In one embodiment, a thermal paste or other substance is inserted between heat fins 403 and the inner surface of inner shells 202 and 203 to enhance thermal coupling.

Figure 5:
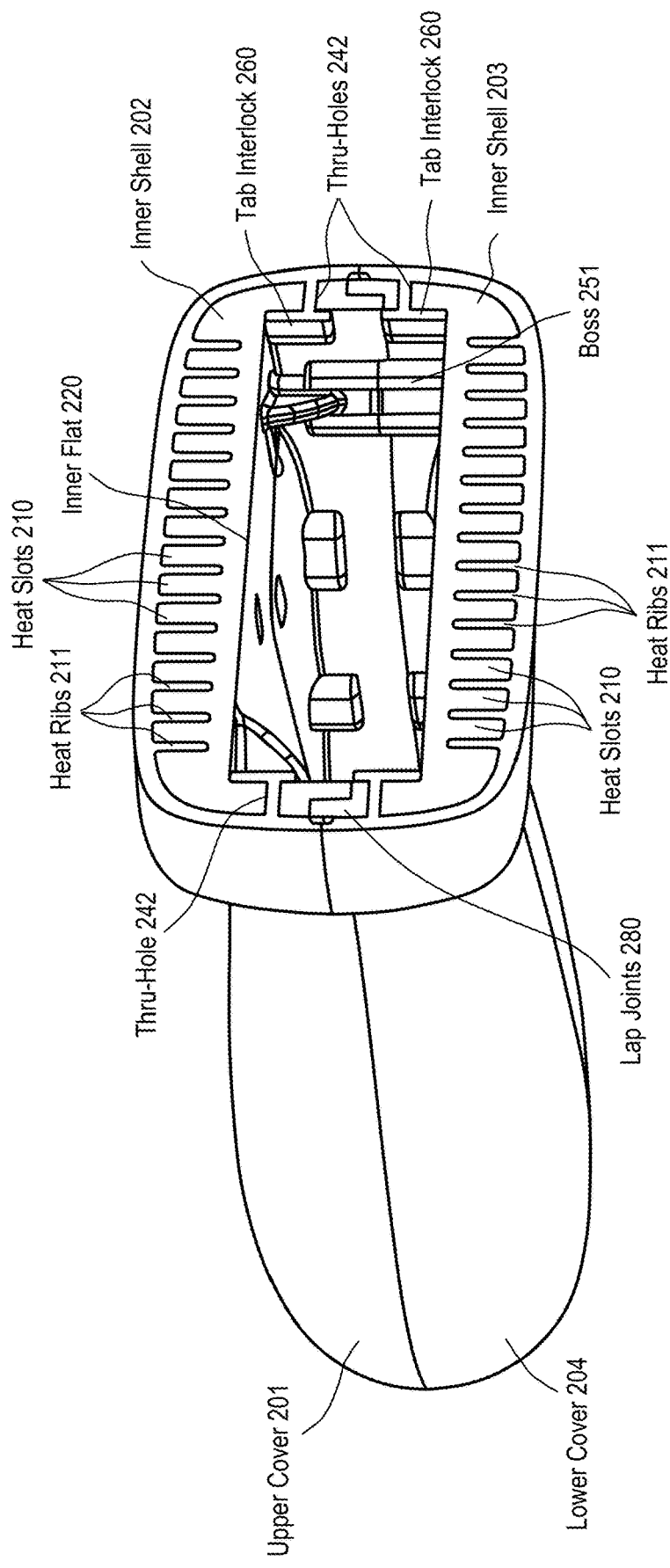
FIG. 5 illustrates the upper half and the lower half of the probe case connected together.

FIG. 5 illustrates the upper half and the lower half of the probe case connected together. Referring to FIG. 5, upper cover 201 and lower cover 204 are connected via lap joints 280 on inner shells 202 and 203. Examples of mechanical interlocks between the outer case (formed by upper cover 201 and lower cover 204) and the inner enclosure (formed by inner shells 202 and 203) are illustrated via thru-holes 242 and tab interlocks 260. Also illustrated is the mating between heat ribs 211 of the outer cover formed by upper cover 201 and lower cover 204 and the heat rib slots 210 of the inner enclosure formed by inner shells 202 and 203. As shown in FIG. 5, an inner shell 202 has an inner flat 220.

In one embodiment, RTV (room temperature vulcanized) sealant is used around the coupling of outer cover 201 and outer cover 204. Instead of using an RTV sealant around the sides, a gasket could be used.

Figures 6B, 7B:
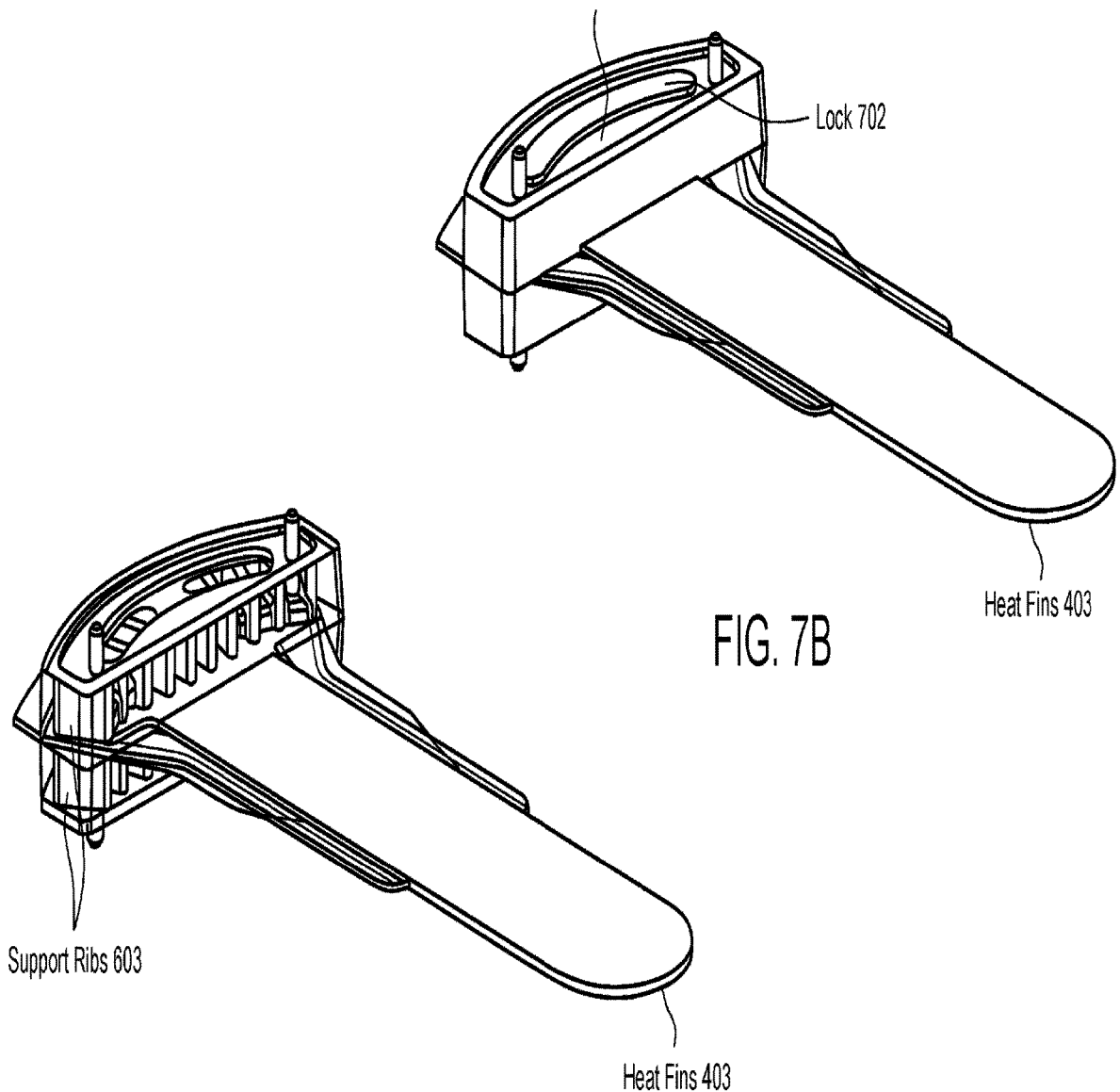

FIGS. 6A-6B and 7A-7B illustrate embodiments of the backing block with heat fins. Referring to FIGS. 6A and 6B, heat fins 403 are coupled with signal flex circuits 601. In one embodiment, two heat fins 403 and two signal flexes 601 are pre-bonded in a backing block region and sandwiched together at the midsection with no gaps in-between. In one embodiment, the prebonding is performed using an adhesive. In on embodiment, the bonded configuration of heat fins 403 and signal flexes 601 is coupled to extension 604. In one embodiment, extension 604 comprises of the thermally conducted material such as, for example copper, aluminum, etc. Extension 604 abuts support ribs 603.

Return planes 602 include holes for alignment with pins 405 and rest on support ribs 603. Support ribs 603 include a number of rib blocks (e.g., rectangular blocks) coupled together with smaller blocks such as the upper blocks extend beyond the inner blocks that couple them together. In one embodiment, support ribs 603 are pre-molded, support return planes, allow low-pressure injection molding flow, and provide structural and resist from the shrink of resin.

In one embodiment, the transducer array (e.g., array 404 of FIG. 4) undergoes low pressure injection molding to create backing block 710. The low pressure injection molding of backing block 710 eliminates labor-intensive hand casting. In one embodiment, the center sandwich of the flex circuits 601 and heat fins 403 are injection molded with the pre-molded plastic support ribs 603. Both the sandwiched flex circuits and heat fins are retained at the mold parting line.

Backing block 710 also includes an exposed outer return ground planes 701. In one embodiment, plastic locks 702 locks in ground plane 701. In one embodiment, lock 702 is overmolded plastic lock. In one embodiment, exposed ground plane 701 (e.g., copper ground plane) mates with a conductive elastomer gasket (e.g., gasket 401 of FIG. 4) for direct EMC to the inner enclosure (i.e., shells 202 and 203. In this way, no solder tails or copper foil is needed.

Figure 8A:
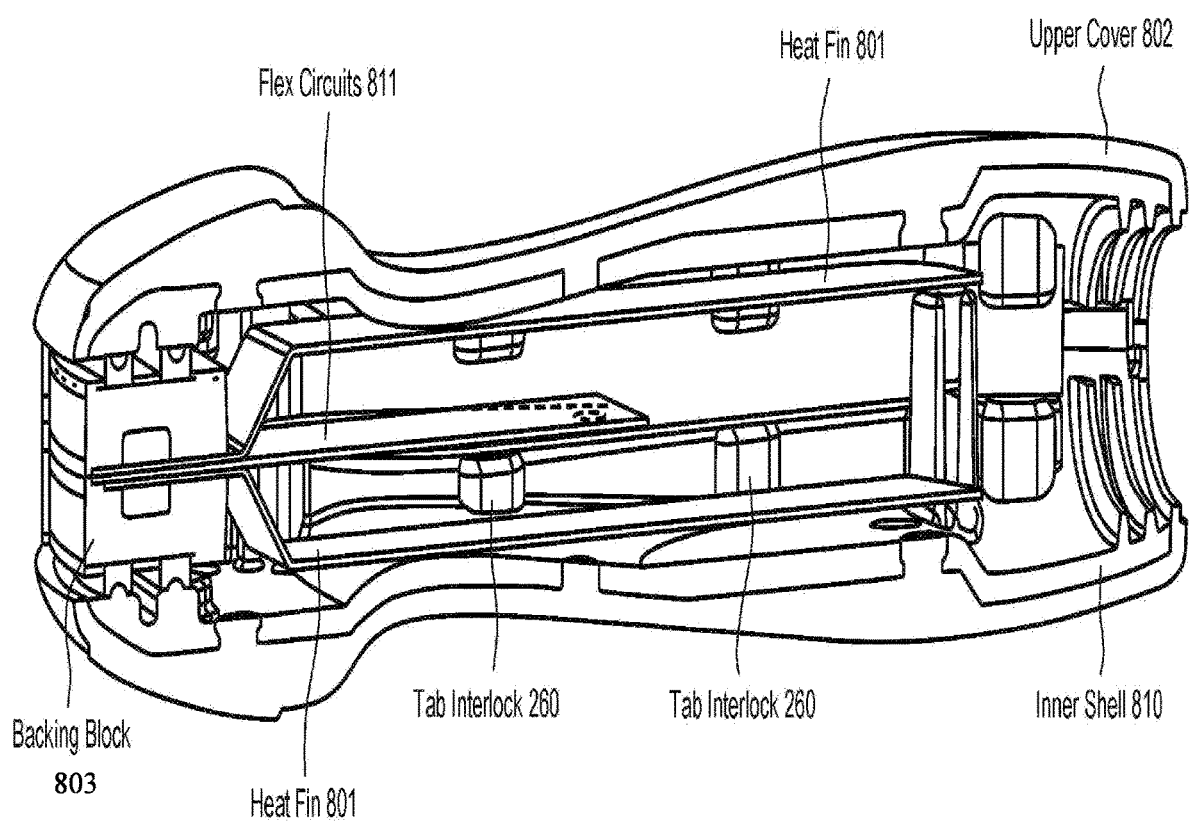
FIG. 8A illustrates a side section view of one embodiment of a probe case with thermal fins.
Figure 8B:
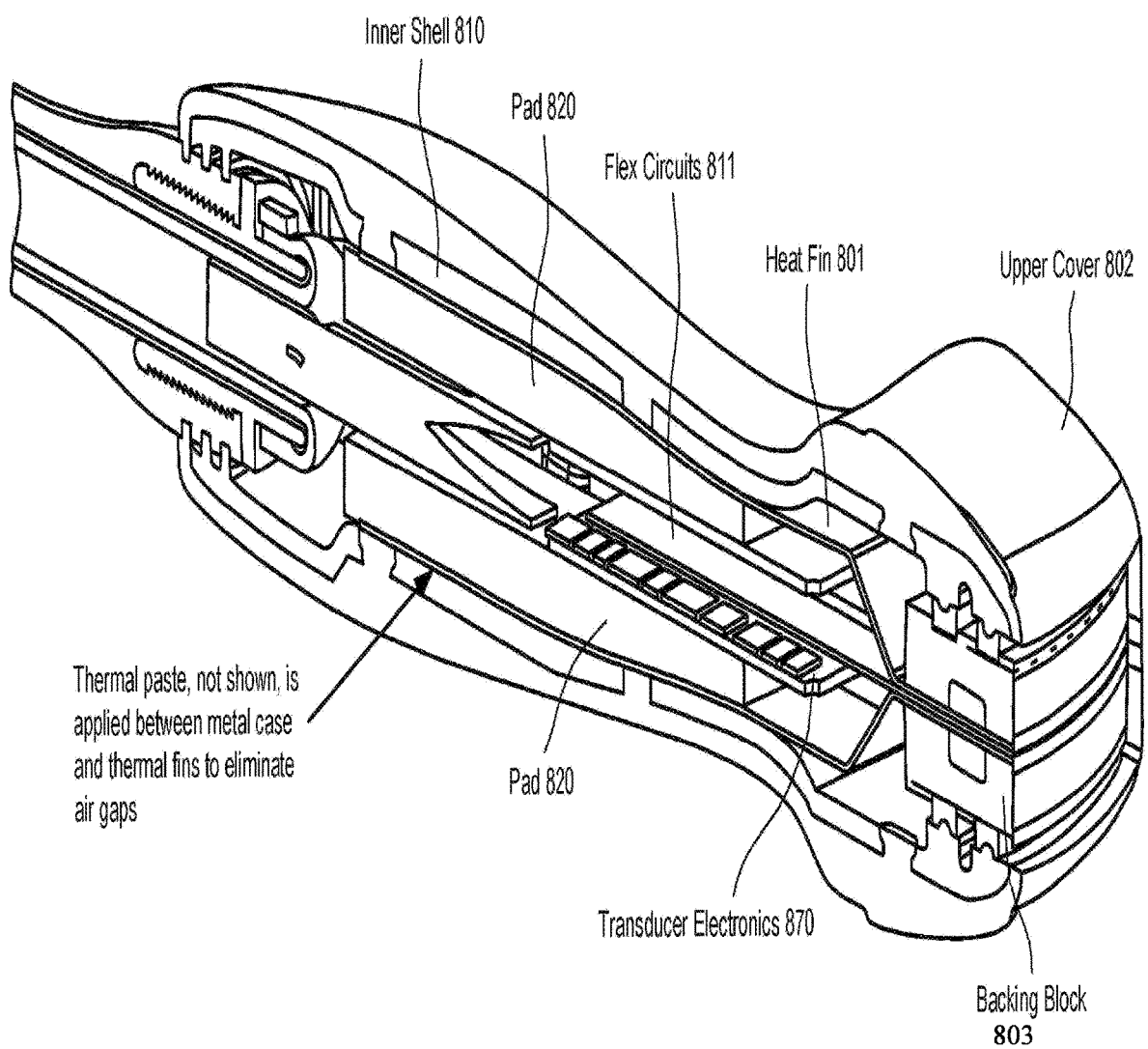
FIG. 8B illustrates a side section view of one embodiment of a probe case with thermal fins and pads to force the fins into contact with an inner shell.

FIG. 8A illustrates a side section view of one embodiment of a probe case with thermal fins. Referring to FIG. 8A, backing block 803 is shown coupled to heat fins 801 and flex circuits 811. As shown in FIGS. 8A and 8B, the probe case includes an upper cover 802. As shown in FIG. 8B, pads 820 are inserted between flex circuits 811 (and other centrally located electronics) and heat fins 801, thereby forcing heat fins 801 against the inner surfaces of inner shell 810 (e.g., shells 202 and 203). In one embodiment, the pads are elastomer pads. Where inner shell 810 (e.g., inner shells 202 and 203) comprises of metallic material, heat fins 801 are forced against the metal inner case, and in this combination, the metal inner case offers a large surface contact with long thermal fins to enhance thermal transfer. In one embodiment, a thermal paste is applied between the metal case and the thermal fins as a way to eliminate air gaps which is detrimental to thermal transfer.

FIG. 8B illustrates a side section view of one embodiment of a probe case of FIG. 8A that illustrates elastomer pads to force the fins into contact with an inner shell. Referring to FIG. 8B, elastomer pads 820 are shown forcing heat fins 801 against the inner surfaces of inner shell 801 (e.g., shells 202 and 203). As discussed above, thermal paste is used to thermally connect thermal fins 801 to inner shell 801. Note also that FIG. 8B illustrates transducer electronics 870 (e.g., printed circuit boards (PCBs), etc.) associated with the transducer array coupled the cable of the probe.

Figure 9:
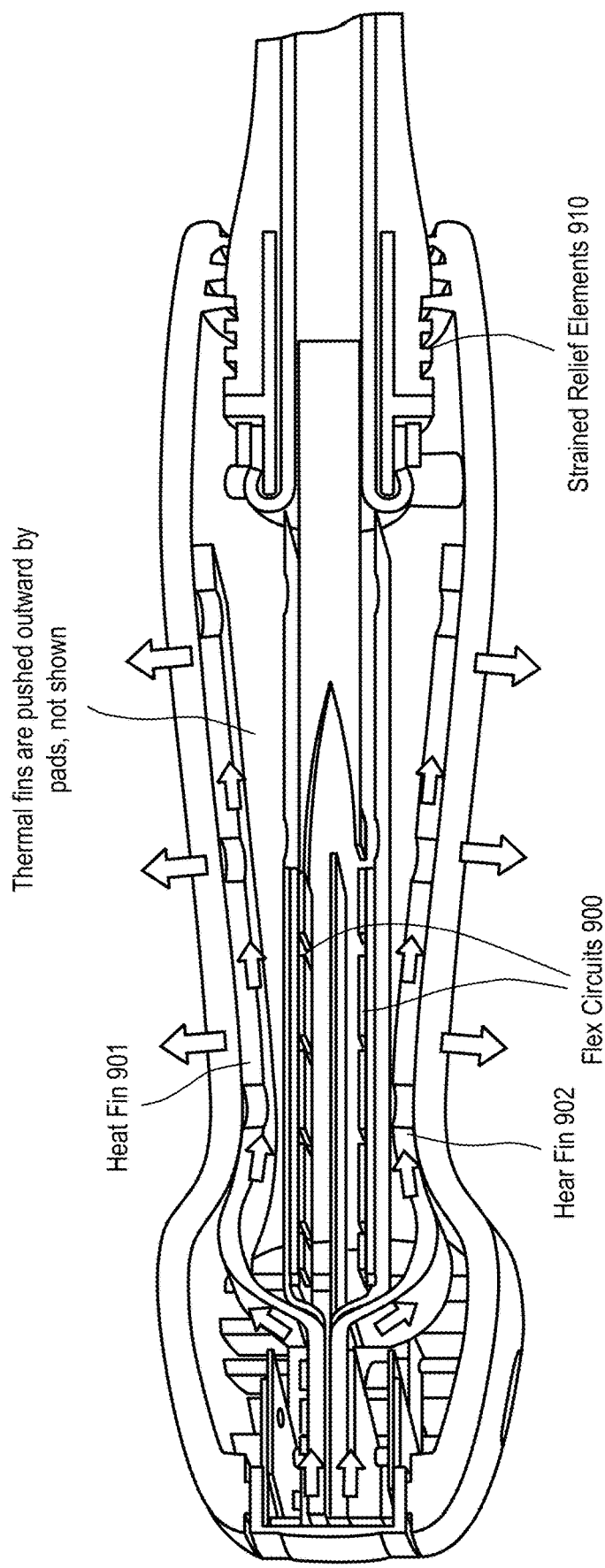
FIG. 9 illustrates a side section view of another embodiment of a probe case with thermal fins.

FIG. 9 illustrates a side section view of another embodiment of a probe case with thermal fins. Referring to FIG. 9, the cable from a cable assembly is coupled to signal flex circuits 900. The cable has a metal woven mesh buried along its entire length for shielding. During assembly, a portion of this woven mesh near the strain relief element 910 is peeled back from the cable and touches the two halves of the inner shell to enclose the probe as shown. Note that heat fins 901 and 902 are pushed into thermal contact with the inner surfaces of the inner metal enclosure and transfers heat as shown by the arrows.

Figure 10:
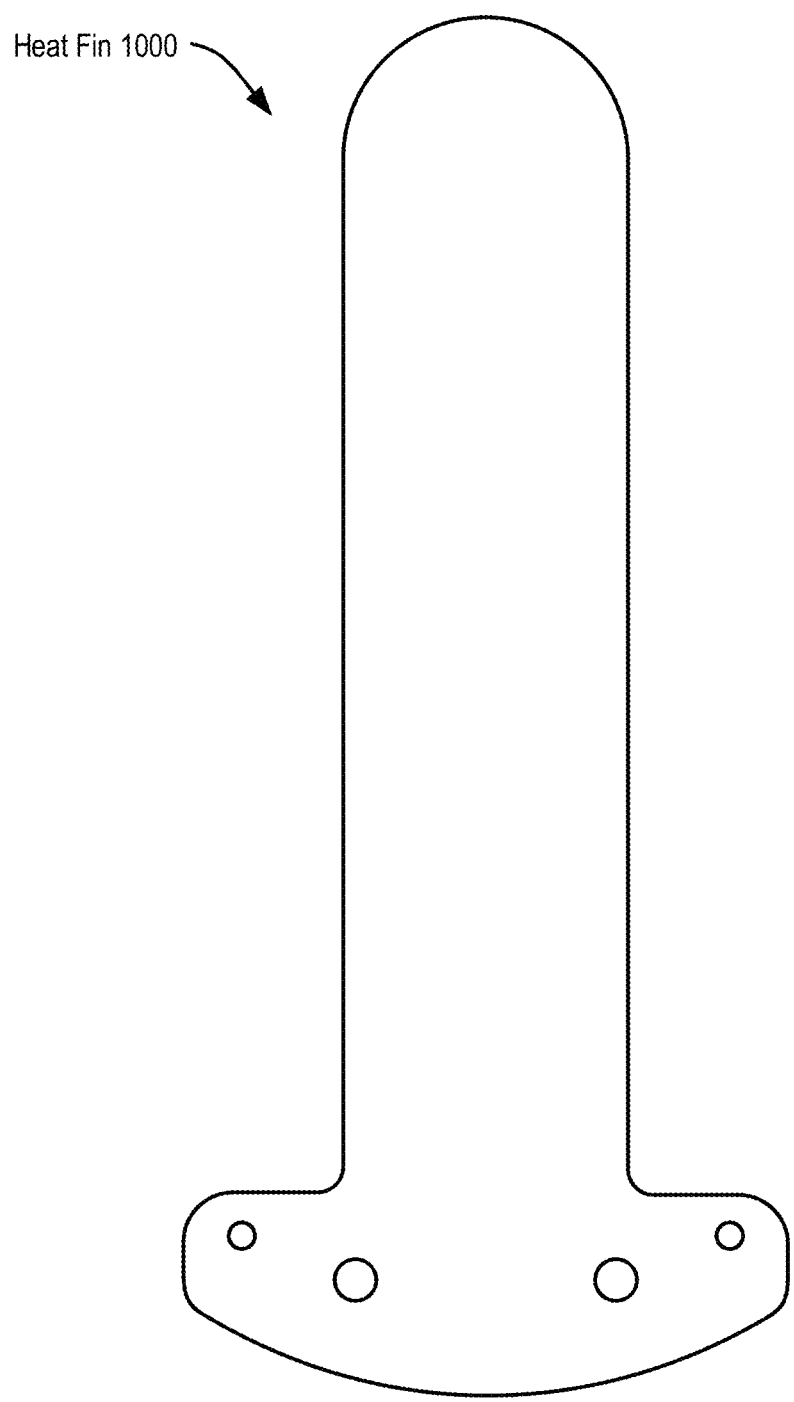
FIG. 10 illustrates one embodiment of a heat fin.

FIG. 10 illustrates one embodiment of a heat fin. Referring to FIG. 10, in one embodiment, heat fin 1000 has a width of 1.48 inches at its widest point, which would be contained in the backing block (e.g., backing block 710). Heat fin 1000 also has an extension that extends from the backing block. In one embodiment, the width of the extension is 0.70 inches and a length as measured from pins (e.g., pins 405) in the backing block of 3.00 inches. Note that other sizes of heat fins may be used.

While FIG. 10 illustrates one embodiment of a heat fin and its shape, heat fins may have other shapes. For example, in one embodiment, the portion of the heat fin that extends through the probe handle may have different dimensions. In other words, the portion of the heat fin that extends through the probe wouldn't have a uniform shape such as shown in FIG. 10. For example, the extension of the heat fin may have a first portion and a second portion, wherein the dimensions of the first portion are different than the second portion. Furthermore, while the heat fin depicted in FIG. 10 is uniform in shape, particularly the extension, this is not required. Each heat fin may have various shapes and sizes that are based on the internal components and features of the probe. For example, a heat fin may have contours, cut-out areas, and/or shaped features that are needed to avoid contact with internal components in the probe while still providing the necessary thermal path through the probe. In yet another embodiment, the shape of a heat fin is designed to coincide and contact one or more internal electrical components that generate heat within the probe to improve, and potentially optimize, the thermal transfer within, and ultimately to the exterior of, the probe.

In one embodiment, the thickness of each heat fin ranges from 0.005" to 0.050" (e.g., 0.010"). Note that heat fins of other thicknesses may be used and their size selected based on the desired thermal transfer properties of the heat fins, the desired amount of heat reduction at the transducer face, and space limitations within the probe itself (e.g., the size of the inner cavity of the probe).

In another alternative embodiment, the heat fin has multiple layers of the same material (e.g., copper). Furthermore, in one embodiment, the thickness of the heat fin changes from one portion of the heat fin to the next. For example, one portion of the heat fin may have one thickness while another portion or portions of the heat fin have a different thickness. In one embodiment, the heat fin has a thicker section embedded within the transducer near the lens, with a thinner portion of the heat fin extending outward from the transducer array into the handle area. Thus, the thickness of the heat fin changes from a first portion and a second portion.

In one embodiment, the thicker section is metal or ceramic diecast, investment cast, CNC, etc. The use of multi-layers can provide additional thermal transfer benefits.

In yet another alternative embodiment, the heat fin has various sized portions, such as described above, and multiple layers, where there are different combinations of layers used in the different portions of the heat fin. For example, in one embodiment, the portion of the heat fin in the lens portion has more layers than in the handle portion, thereby appearing to taper off as the heat fin extends into the probe handle. In another embodiment, the portion of the heat fin in the lens portion has fewer layers than in the handle portion, such that the heat fin grows in size as the heat fin extends into the probe handle.

Figure 11:
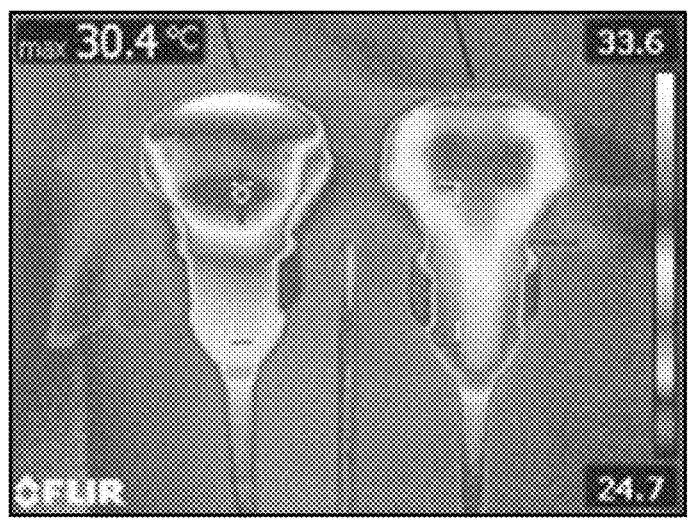
FIGS. 11-13 illustrate thermal images of probes of the prior art and probes utilizing the techniques described herein.
Figure 12:
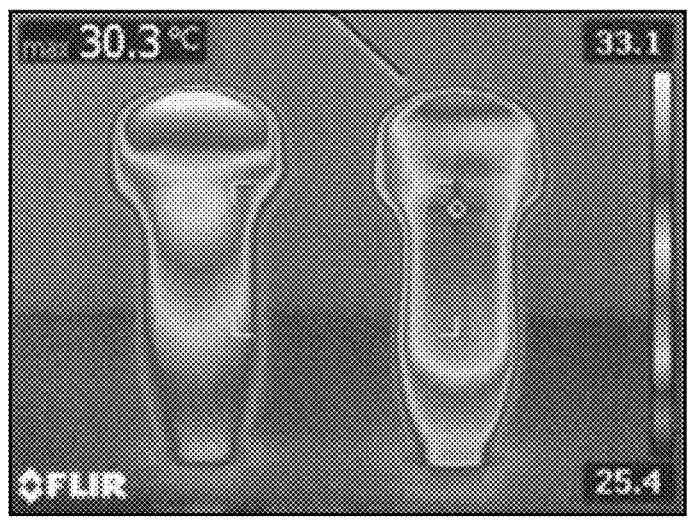
Figure 13:
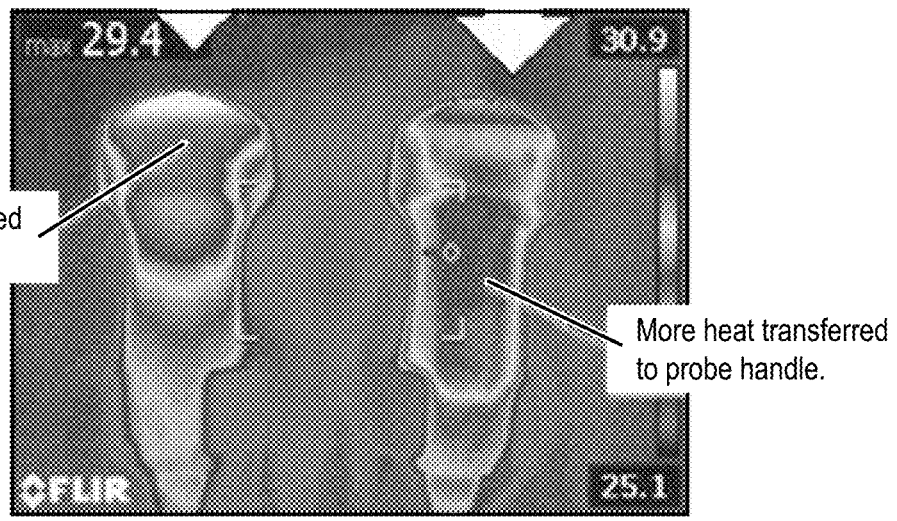

FIGS. 11-13 illustrate thermal images of probes of the prior art and probes utilizing the techniques described herein. Referring to each of FIGS. 11-13, a pair of probes is shown with a prior art probe configuration on the left and a probe constructed with features disclosed above on the right. Note that in each instance, the thermal energy spreads into and dissipates more into the probe handle in the case of the probes on the right with features disclosed herein in comparison to the probes on the left.

There is a number of example embodiments described herein.

Example 1 is a ultrasound transducer probe comprising: a probe array assembly having a probe tip; a first enclosure disposed around a portion of the probe array assembly, the first enclosure having first and second openings and comprising a thermally conductive material; and one or more thermally conductive fins contained within the first enclosure, each of the one or more thermally conductive fins having one end enclosed within the probe array assembly and a portion extending away from the probe array assembly and in thermal contact with an inner surface of the first enclosure to create a thermal path from the first opening to the second opening in the first enclosure.

Example 2 is the ultrasound transducer probe of example 1 that may optionally include that the one or more thermally conductive fins comprises metal.

Example 3 is the ultrasound transducer probe of example 1 that may optionally include a plurality of material pieces to force the one or more thermally conductive fins toward with the inner surface of the first enclosure.

Example 4 is the ultrasound transducer probe of example 3 that may optionally include thermal paste thermally coupling the one or more thermally conductive fins with the inner surface of the first enclosure.

Example 5 is the ultrasound transducer probe of example 3 that may optionally include that the plurality of material pieces comprises a plurality of pads.

Example 6 is the ultrasound transducer probe of example 1 that may optionally include a second enclosure disposed around the first enclosure.

Example 7 is the ultrasound transducer probe of example 6 that may optionally include that the second enclosure comprises a non-electrically conductive material.

Example 8 is the ultrasound transducer probe of example 6 that may optionally include that the first enclosure comprises first and second clamshell halves and the second enclosure comprise third and fourth clamshell halves, wherein the third clamshell half of the second enclosure is coupled to the first clamshell half of the first enclosure using mechanical interlocks, wherein the fourth clamshell half of the second enclosure is coupled to the second clamshell half of the first enclosure using mechanical interlocks.

Example 9 is the ultrasound transducer probe of example 8 that may optionally include that the first and second clamshell halves comprise a plurality of thru-holes, and non-electrically conductive material forming the third and fourth clamshell halves extends into and forms overlaps onto interior surfaces of the first and second clamshell halves.

Example 10 is the ultrasound transducer probe of example 6 that may optionally include that the first and second clamshell halves are coupled together via lap joints along sides of the first and second clamshell halves.

Example 11 is the ultrasound transducer probe of example 6 that may optionally include heat ribs protruding from the inner surface of the third clamshell half extend into and mate with slots of the first clamshell half and heat ribs protruding from the inner surface of the fourth clamshell half extend into and mate with slots of the second clamshell half.

Example 12 is the ultrasound transducer probe of example 1 that may optionally include one or more electrically conductive electromagnetic interference (EMI) gaskets coupled to one or more return planes of the probe array assembly, the one or more electrically conductive EMI gaskets coupled to inner surfaces of the first enclosure.

Example 13 is the ultrasound transducer probe of example 12 that may optionally include that one or more EMI gaskets provide a direct contact from the one or more return planes to the inner surfaces of the first enclosure.

Example 14 is the ultrasound transducer probe of example 12 that may optionally include that the first enclosure comprises metal and comprises overlapping joints and operates with the EMI gaskets to create a full Faraday cage except for the first and second openings.

Example 15 is the ultrasound transducer probe of example 14 that may optionally include that the second opening of the first enclosure is operable to electrically connect and provide a thermal coupling to a metal woven mesh of a cable enclosure.

Example 16 is an ultrasound transducer probe comprising: a probe array assembly having a probe tip; a first enclosure disposed around a portion of the probe array assembly, the first enclosure having first and second openings and comprising wherein the first enclosure comprises first and second metal clamshell halves coupled together via lap joints along sides of the first and second clamshell halves; a second enclosure disposed around the first enclosure and having third and fourth clamshell halves, wherein the third clamshell half of the second enclosure is coupled to the first clamshell half of the first enclosure using mechanical interlocks, wherein the fourth clamshell half of the second enclosure is coupled to the second clamshell half of the first enclosure using mechanical interlocks; one or more thermally conductive fins contained within the first enclosure and comprising metal, each of the one or more thermally conductive fins having one end enclosed within the probe array assembly and a portion extending away from the probe array assembly and in thermal contact with an inner surface of the first enclosure to create a thermal path from the first opening to the second opening in the first enclosure; and one or more electrically conductive electromagnetic interference (EMI) gaskets coupled to one or more return planes of the probe array assembly, the one or more electrically conductive EMI gaskets coupled to inner surfaces of the first enclosure to provide direct contact from the one or more return planes to the inner surfaces of the first enclosure to create a full Faraday cage with exception of the first and second openings.

Example 17 is the probe of example 16 that may optionally include a plurality of material pieces to force the one or more thermally conductive fins toward with the inner surface of the first enclosure.

Example 18 is the probe of example 16 that may optionally include that the first and second clamshell halves comprise a plurality of thru-holes, and non-electrically conductive material forming the third and fourth clamshell halves extends into and forms overlaps onto interior surfaces of the first and second clamshell halves.

Example 19 is the probe of example 16 that may optionally include that the second enclosure comprises a non-electrically conductive material, and further wherein the third clamshell half of the second enclosure is overmolded onto the first clamshell half of the first enclosure using mechanical interlocks, wherein the fourth clamshell half of the second enclosure is overmolded onto the second clamshell half of the first enclosure.

Example 20 is the probe of example 16 that may optionally include that the second opening of the first enclosure is operable to electrically connect and provide a thermal coupling to a metal woven mesh of a cable enclosure.

Example 21 is the probe of example 16 that may optionally include a plurality of bosses connecting the first and second clamshell halves together.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in themselves recite only those features regarded as essential to the invention.

We claim:

1. An ultrasound transducer probe comprising:
a probe array assembly having a probe tip;
a first enclosure disposed around a portion of the probe array assembly, the first enclosure having first and second openings and comprising a thermally conductive material;
one or more thermally conductive fins contained within the first enclosure, each of the one or more thermally conductive fins having a first end portion enclosed within the probe array assembly and a second end portion extending away from the probe array assembly in a first plane and in thermal contact with an inner surface of the first enclosure to create a thermal path from the first opening to the second opening in the first enclosure, the one or more thermally conductive fins comprising a first fin having a first side and a second side opposite to the first side;

a flex circuit attached to the first end of the first fin and extending in a second plane that is a first distance away from the first plane; and a first elastomer pad on the first side between the second end of the first fin and the flex circuit, wherein the second side of the second end of the first fin is forced, by the first elastomer pad, toward and into contact with the inner surface of the first enclosure and away from the second plane to increase the first distance to transfer heat from the probe tip through a path between the first fin and the inner surface of the first enclosure.

2. The probe of claim 1, wherein the first fin comprises a metal.

3. The probe of claim 1, further comprising:
a thermal paste thermally coupling the one or more thermally conductive fins with the inner surface of the first enclosure.

4. The probe of claim 1, further comprising:
a second fin comprising a proximal end portion attached to the flex circuit and a distal end portion extending in a third plane that is a second distance away from the second plane, and a second elastomer pad between the distal end portion of the second fin and the flex circuit, wherein the distal end portion of the second fin is forced, by the second elastomer pad, toward the inner surface of the first enclosure and away from the second plane to increase the second distance to transfer heat from the probe tip through a path between the second fin and the inner surface of the first enclosure.

5. The probe of claim 1, further comprising:
a second enclosure disposed around the first enclosure, the second enclosure comprising heat ribs extending to the first enclosure, wherein the heat ribs are sized to transfer a predetermined amount of heat expected to be produced based on frequency of operation of the ultrasound transducer probe.

6. The probe of claim 1, wherein the second end portion is electrically connected and provides a thermal coupling to a metal woven mesh of a cable enclosure.

7. An ultrasound transducer probe comprising:
a probe array assembly having a probe tip;
a first enclosure disposed around a portion of the probe array assembly, the first enclosure having first and second openings and wherein the first enclosure comprises first and second metal clamshell halves coupled together via lap joints along sides of the first and second clamshell halves;
a second enclosure disposed around the first enclosure and having third and fourth clamshell halves, wherein the third clamshell half of the second enclosure is coupled to the first clamshell half of the first enclosure using mechanical interlocks, wherein the fourth clamshell half of the second enclosure is coupled to the second clamshell half of the first enclosure using mechanical interlocks;
one or more thermally conductive fins contained within the first enclosure and comprising metal, each of the one or more thermally conductive fins having a first end portion enclosed within the probe array assembly and a second end portion extending away from the probe array assembly in a first plane and in thermal contact with an inner surface of the first enclosure to create a thermal path from the first opening to the second opening in the first enclosure, the one or more thermally conductive fins comprising a first fin having a first side and a second side opposite to the first side;

a flex circuit attached to the first end of the first fin and extending in a second plane that is separated from the first plane by a space;

a first elastomer pad on the first side in the space between the second end of the first fin and the flex circuit, wherein the second side of the second end of the first fin is forced, by the first elastomer pad, toward and into contact with the inner surface of the first enclosure and away from the second plane to increase the first distance to transfer heat from the probe tip through a path between the first fin and the inner surface of the first enclosure;

and one or more electrically conductive electromagnetic interference (EMI) gaskets coupled to one or more return planes of the probe array assembly, the one or more electrically conductive EMI gaskets coupled to inner surfaces of the first enclosure to provide direct contact from the one or more return planes to the inner surfaces of the first enclosure to create a full Faraday cage with exception of the first and second openings.

8. The probe of claim 7, wherein the second end portion is electrically connected and provides a thermal coupling to a metal woven mesh of a cable enclosure.

9. The probe of claim 1, wherein the probe array assembly comprises a backing block, wherein the first end portion of the first fin and a first portion of the flex circuit attached to the first end portion are embedded in the backing block.

10. The probe of claim 1, wherein the one or more thermally conductive fins comprises a second fin attached to the flex circuit that is between the second fin and the first fin with no air gap in between.

11. The probe of claim 1, wherein the probe array assembly comprises a backing block, and further wherein the first end portion that is a widest portion of the first fin and is retained in the backing block.

12. The probe of claim 1, wherein the first fin has at least one of a contour, a cut-out area, or a shaped feature to avoid contact with at least one component in the probe.

13. The probe of claim 1, wherein the first fin has a shape that is configured to contact with one or more internal components in the probe.

14. The probe of claim 1, wherein the first end portion comprises a first plurality of layers and the second end portion comprises a second plurality of layers that is different in number to the first plurality.

15. The probe of claim 1, wherein the first and second end portions have different thicknesses.

16. The probe of claim 1, wherein the probe is configured to communicate with an ultrasound imaging system.

17. The probe of claim 7, further comprising:
a second fin comprising a proximal end portion attached to the flex circuit and a distal end portion extending in a third plane that is a second distance away from the second plane, and a second elastomer pad between the distal end portion of the second fin and the flex circuit, wherein the distal end portion of the second fin is forced, by the second elastomer pad, toward the inner surface of the first enclosure and away from the second plane to increase the second distance to transfer heat from the probe tip through a path between the second fin and the inner surface of the first enclosure.

18. The probe of claim 7, further comprising:
a second enclosure disposed around the first enclosure, the second enclosure comprising heat ribs extending to the first enclosure wherein the heat ribs are sized to transfer a predetermined amount of heat expected to be produced based on frequency of operation of the ultrasound transducer probe.

19. The probe of claim 7, wherein the probe array assembly comprises a backing block, and wherein the first end portion of the first fin and a first portion of the flex circuit attached to the first end portion are embedded in the backing block.

\* \* \* \* \*